(12) United States Patent
Currie

(10) Patent No.: US 8,598,087 B2
(45) Date of Patent: Dec. 3, 2013

(54) CRYSTALLINE FORM OF 4-[5-[3-CHLORO-5-(TRIFLUOROMETHYL) PHENYL]-4, 5-DIHYDRO-5-(TRIFLUOROMETHYL)-3-ISOXAZOLYL]-N-[2-0X0-2-[(2,2,2-TRIFLUOROETHYL)AMINO]ETHYL]-1-NAPH-THALENECARBOXAMIDE

(75) Inventor: Martin James Currie, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 13/700,222

(22) PCT Filed: May 19, 2011

(86) PCT No.: PCT/US2011/037083
§ 371 (c)(1),
(2), (4) Date: Feb. 18, 2013

(87) PCT Pub. No.: WO2011/149749
PCT Pub. Date: Dec. 1, 2011

(65) Prior Publication Data
US 2013/0137735 A1 May 30, 2013

Related U.S. Application Data

(60) Provisional application No. 61/348,958, filed on May 27, 2010.

(51) Int. Cl.
*A01N 43/80* (2006.01)
*C07D 261/02* (2006.01)

(52) U.S. Cl.
USPC .......................................... 504/271; 548/240

(58) Field of Classification Search
None
See application file for complete search history.

(56) References Cited

U.S. PATENT DOCUMENTS

| | | |
|---|---|---|
| 2,891,855 A | 6/1959 | Hans et al. |
| 3,060,084 A | 10/1962 | Littler |
| 3,235,361 A | 2/1966 | Loux |
| 3,299,566 A | 1/1967 | MacMullen |
| 3,854,216 A | 12/1974 | Baxter et al. |
| 3,879,532 A | 4/1975 | Hass et al. |
| 3,920,442 A | 11/1975 | Albert et al. |
| 3,950,360 A | 4/1976 | Atsushi et al. |
| 3,984,564 A | 10/1976 | Atsushi et al. |
| 4,129,568 A | 12/1978 | Howe |
| 4,144,050 A | 3/1979 | Frensch et al. |
| 4,172,714 A | 10/1979 | Albert |
| 4,199,569 A | 4/1980 | Chabala et al. |
| 4,224,901 A | 9/1980 | Carey |
| 4,311,857 A | 1/1982 | Nagabhushan |
| 4,582,918 A | 4/1986 | Nagabhushan et al. |
| 4,743,700 A | 5/1988 | Giancarlo et al. |
| 4,876,352 A | 10/1989 | Schumacher et al. |
| 4,916,154 A | 4/1990 | Asato et al. |
| 4,973,750 A | 11/1990 | Nagabhushan et al. |
| 5,089,480 A | 2/1992 | Gibson et al. |
| 5,105,009 A | 4/1992 | Giancarlo et al. |
| 5,180,587 A | 1/1993 | Moore |
| 5,184,573 A | 2/1993 | Stevens, Jr. |
| 5,208,030 A | 5/1993 | Hoy et al. |
| 5,227,494 A | 7/1993 | Schumacher et al. |
| 5,232,701 A | 8/1993 | Ogawa et al. |
| 5,288,710 A | 2/1994 | Cvetovich |
| 5,352,832 A | 10/1994 | Wu et al. |
| 5,382,673 A | 1/1995 | Clark et al. |
| 5,399,717 A | 3/1995 | Cvetovich et al. |
| 5,555,848 A | 9/1996 | Trujillo et al. |
| 5,567,844 A | 10/1996 | Giancarlo et al. |
| 5,663,361 A | 9/1997 | Towson et al. |
| 5,958,888 A | 9/1999 | Macy et al. |
| 6,054,434 A | 4/2000 | Kropp et al. |
| 6,239,112 B1 | 5/2001 | Macy et al. |
| 6,270,768 B1 | 8/2001 | O'Connell et al. |
| 6,271,255 B1 | 8/2001 | Leadlay et al. |
| 6,339,063 B1 | 1/2002 | Kropp et al. |
| 6,437,151 B2 | 8/2002 | Leadlay et al. |
| 6,472,371 B1 | 10/2002 | Dirlam et al. |
| 6,514,945 B1 | 2/2003 | Boettner |
| 6,603,044 B1 | 8/2003 | Tohnishi et al. |
| 6,645,984 B2 | 11/2003 | Braun et al. |
| 6,747,047 B2 | 6/2004 | Lahm et al. |
| 7,662,972 B2 | 2/2010 | Mita et al. |
| 7,897,630 B2 | 3/2011 | Lahm et al. |

(Continued)

FOREIGN PATENT DOCUMENTS

| | | |
|---|---|---|
| CA | 2252543 | 11/1997 |
| CA | 2558848 | 9/2005 |

(Continued)

OTHER PUBLICATIONS

Konno et al., "Palladium-Catalyzed Regio- and Stereoselective Formate Reduction of Fluorine-Containing Allylic Mesylates, A New Entry for the Construction of a Tertiary Carbon Attached with a Fluoroalkyl Group," Journal of Organic Chemistry (2006) 71(9):3545-3550.

(Continued)

*Primary Examiner* — Alicia L Otton
(74) *Attorney, Agent, or Firm* — Pepper Hamilton LLP

(57) ABSTRACT

Disclosed is a solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (Compound 1). Also disclosed are compositions containing a solid form of Compound 1 and methods for controlling an invertebrate pest comprising contacting the invertebrate pest or its environment with a biologically effective amount of a solid form of Compound 1 or a composition containing a solid form of Compound 1.

7 Claims, 1 Drawing Sheet

(56) References Cited

U.S. PATENT DOCUMENTS

| | | | |
|---|---|---|---|
| 7,947,715 | B2 | 5/2011 | Mita et al. |
| 7,951,828 | B1 | 5/2011 | Mita et al. |
| 8,022,089 | B2 | 9/2011 | Mita et al. |
| 8,138,213 | B2 | 3/2012 | Mita et al. |
| 8,217,180 | B2 | 7/2012 | Annis et al. |
| 8,231,888 | B2 | 7/2012 | Lahm et al. |
| 2003/0064939 | A1 | 4/2003 | Sklavounos et al. |
| 2004/0082553 | A1 | 4/2004 | Boojamra et al. |
| 2005/0250822 | A1 | 11/2005 | Mita et al. |
| 2007/0066617 | A1 | 3/2007 | Mita et al. |
| 2009/0023923 | A1 | 1/2009 | Mizukoshi et al. |
| 2009/0133319 | A1 | 5/2009 | Lahm et al. |
| 2009/0143410 | A1 | 6/2009 | Patel |
| 2010/0137612 | A1 | 6/2010 | Yaosaka et al. |
| 2010/0173948 | A1 | 7/2010 | Lahm et al. |
| 2010/0179195 | A1 | 7/2010 | Lahm et al. |
| 2010/0249424 | A1 | 9/2010 | Annis et al. |
| 2010/0254959 | A1 | 10/2010 | Lahm et al. |
| 2010/0254960 | A1 | 10/2010 | Long et al. |
| 2011/0059988 | A1 | 3/2011 | Heckeroth et al. |

FOREIGN PATENT DOCUMENTS

| | | |
|---|---|---|
| CN | 101346336 | 1/2009 |
| DE | 3246493 | 6/1984 |
| EA | 000924 | 6/2000 |
| EP | 1538138 | 6/2005 |
| EP | 1731512 | 12/2006 |
| EP | 1975149 | 10/2008 |
| EP | 2172462 | 4/2010 |
| EP | 1973888 | 1/2011 |
| GB | 2095558 | 10/1982 |
| GB | 2351081 | 12/2000 |
| JP | 199859944 | 3/1998 |
| JP | 1999503114 | 3/1999 |
| JP | 2004529130 | 9/2004 |
| JP | 2005272452 | 10/2005 |
| JP | 2007016017 | 1/2007 |
| JP | 2007106756 | 4/2007 |
| KZ | 13246 | 7/2003 |
| KZ | 16356 | 10/2005 |
| RU | 99101948 | 10/2001 |
| RU | 2433123 | 11/2011 |
| WO | 9113546 | 9/1991 |
| WO | 03015518 | 2/2003 |
| WO | 03024222 | 3/2003 |
| WO | 2004067528 | 8/2004 |
| WO | 200499197 | 11/2004 |
| WO | 2005085216 | 6/2005 |
| WO | 2005094329 | 10/2005 |
| WO | 2006135640 | 12/2006 |
| WO | 2007026965 | 3/2007 |
| WO | 2007070606 | 6/2007 |
| WO | 2007074789 | 7/2007 |
| WO | 2007075459 | 7/2007 |
| WO | 2007079162 | 7/2007 |
| WO | 2007105814 | 9/2007 |
| WO | 2007123855 | 11/2007 |
| WO | 2007125984 | 11/2007 |
| WO | 2008019760 | 2/2008 |
| WO | 2008108448 | 9/2008 |
| WO | 2008122375 | 10/2008 |
| WO | 2008154528 | 12/2008 |
| WO | 2009001942 | 12/2008 |
| WO | 2009002809 | 12/2008 |
| WO | 2009003075 | 12/2008 |
| WO | 2009025983 | 2/2009 |
| WO | 2009035004 | 3/2009 |
| WO | 2009045999 | 4/2009 |
| WO | 2009126668 | 10/2009 |

OTHER PUBLICATIONS

Carey et al., "Advanced Organic Chemistry," 2ed., Part B: Reactions and Synthesis, (1983) Pelenum Press, New York.

Sosnovskii et al., "Ketone-ketone condensation with participation of polyhaloalkyl phenyl ketones," Journal of Organic Chemistry of the USSR, (1992) 28:420-426.

Kamble et al., "An efficient synthesis of pharmacologically active derivatives 1,3,4-Oxadiazoles," Journal of Heterocyclic Chemistry (2006) 43(345):345-352.

Database Chemical Abstracts Service (1988) XP002516318, Database accession No. 111:115084.

Ragaila et al., "Newer heterocycles and carbamates from naphthyl," Egyptian Journal of Pharmaceutical Sciences (1988) 29(1-4):71-87.

Database Chemical Abstracts Service (1996) XP002516333, Database Accession No. 126:31303.

Kuznetsova et al., "Synthesis of fluorine-containing functionalized isoxazolines," Russian Chemical Bulletin (1996) 45 (5):1245-1246.

Dighade et al,. "Effect of solvents in synthesis of new 4-(2-hydroxy-5-methylphenyl)-6-aryl-2-imino-6H-2,3-dihydro-1,3-thiazines," Asian Journal of Chemistry (2001) 13(4):1560-1564.

Lahm et al. (2007): STN International HAPLUS database, Columbus (OH), accession No. 2007:755410.

Motoki et al., "Cooper(I) alkoxide-catalyzed alkynylation of trifluoromethyl ketones," Organic Letters (2007) 9 (16):2997-3000.

Mita et al. (2007): STN International HCAPLUS database, (Columbus, Ohio), Accession No. 2009:740002.

[Kuznetsova et al., "Synthesis of fluorine-containing functionalized isoxazolines," Proceedings of the Academy of Sciences (1996) 5:1306-13071]. English Translation of Russian Office Action received Jul. 3, 2012 attached.

Mita et al. (2007): STN International HCAPLUS database, (Columbus, Ohio), Accession No. 2007:330406.

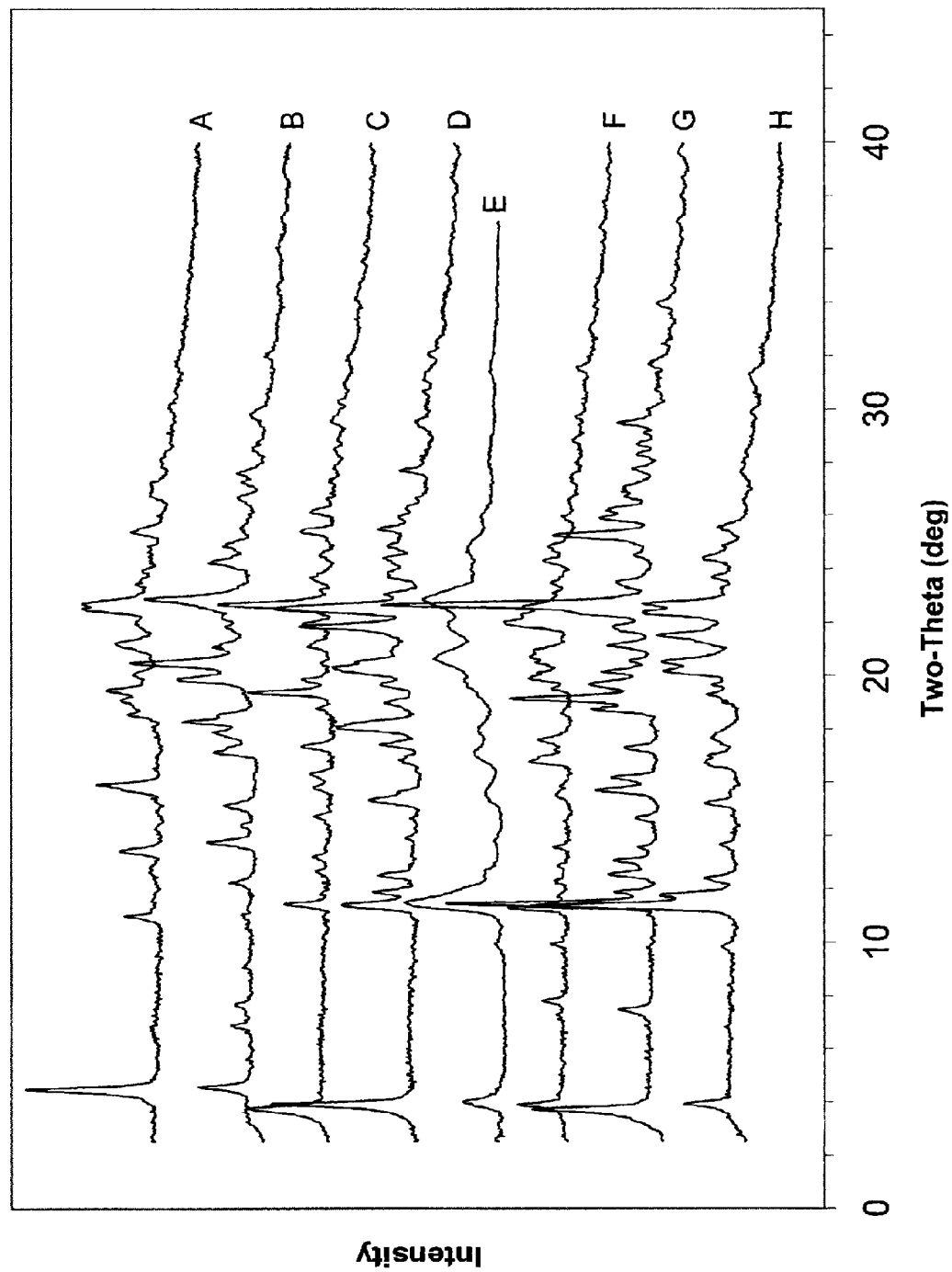

US 8,598,087 B2

CRYSTALLINE FORM OF 4-[5-[3-CHLORO-5-(TRIFLUOROMETHYL) PHENYL]-4, 5-DIHYDRO-5-(TRIFLUOROMETHYL)-3-ISOXAZOLYL]-N-[2-OX0-2-[(2,2,2-TRIFLUOROETHYL)AMINO]ETHYL]-1-NAPH-THALENECARBOXAMIDE

FIELD OF THE INVENTION

This invention relates to a solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

BACKGROUND OF THE INVENTION

The solid state of chemical compounds can be amorphous (i.e. no long-range order in the positions of atoms) or crystalline (i.e. atoms arranged in an orderly repeating pattern). While only one crystal form is known for the solid state of many compounds, polymorphs have been discovered for some compounds. The term "polymorph" refers to a particular crystal form (i.e. structure of crystal lattice) of a chemical compound that can exist in more than one crystal form in the solid state. Polymorphs can differ in such chemical and physical (i.e. physiochemical) properties as crystal shape, density, hardness, color, chemical stability, melting point, hydroscopicity, suspensibility and dissolution rate, and such biological properties as biological availability.

Predicting physiochemical properties such as melting point for a crystal form or crystal forms in which the solid state of a chemical compound can exist remains impossible. Furthermore, even predicting whether the solid state of a compound may be present in more than one crystal form is not possible.

PCT Patent Publication WO 09/002,809 discloses 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide and methods for its preparation, as well as the utility of this compound as an invertebrate pest control agent. A new solid form of this compound has now been discovered.

SUMMARY OF THE INVENTION

This invention relates to a solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (Compound 1). More particularly, this invention is directed to a crystalline polymorph of Compound 1 designated Form B characterized by a powder X-ray diffraction pattern having at least the 2θ reflection positions 17.433, 18.586, 20.207, 20.791, 21.41, 22.112, 23.182, 24.567 and 27.844.

This invention also relates to compositions containing a solid form of Compound 1 and methods for controlling an invertebrate pest comprising contacting the invertebrate pest or its environment with a biologically effective amount of a solid form of Compound 1 or a composition containing a solid form of Compound 1.

BRIEF DESCRIPTION OF THE DRAWINGS

FIG. 1 is the powder X-ray diffraction patterns of polymorph and pseudopolymorph crystal forms of Compound 1 showing absolute intensity count graphed against 2θ reflection positions.

DETAILED DESCRIPTION OF THE INVENTION

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Embodiments of the present invention include:

Embodiment 1

The crystalline solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide wherein at least 90% of the solid form is polymorph Form B.

Embodiment 2

The crystalline solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide wherein at least 80% of the solid form is polymorph Form B.

Embodiment 3

The crystalline solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide wherein at least 70% of the solid form is polymorph Form B.

Embodiment 4

The crystalline solid form of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide wherein at least 60% of the solid form is polymorph Form B.

Embodiment 5

A composition comprising Compound 1, wherein Compound 1 is present in at least 90% polymorph Form B, and at least one additional component selected from the group consisting of surfactants, solid diluents and liquid diluents, said composition optionally further comprising at least one additional biologically active compound or agent.

Embodiment 6

A composition comprising Compound 1, wherein Compound 1 is present in at least 80% polymorph Form B, and at least one additional component selected from the group consisting of surfactants, solid diluents and liquid diluents, said composition optionally further comprising at least one additional biologically active compound or agent.

Embodiment 7

A composition comprising Compound 1, wherein Compound 1 is present in at least 70% polymorph Form B, and at least one additional component selected from the group consisting of surfactants, solid diluents and liquid diluents, said composition optionally further comprising at least one additional biologically active compound or agent.

Embodiment 8

A composition comprising Compound 1, wherein Compound 1 is present in at least 60% polymorph Form B, and at least one additional component selected from the group consisting of surfactants, solid diluents and liquid diluents, said composition optionally further comprising at least one additional biologically active compound or agent.

The crystalline polymorph of Compound 1 designated Form B, and any embodiments of the invention can be used for the protection of an animal from an invertebrate pest by administration of the compound to the animal.

Therefore, the invention is understood to include the crystalline polymorph of Compound 1 designated Form B, or any embodiments of the invention for use as an animal medicament, or more particularly a parasiticidal animal medicament. The medicament may be in any art recognized dosage forms including oral, topical or parenteral dosage forms.

The invention is also understood to include the use of the crystalline polymorph of Compound 1 designated Form B, or any embodiments of the invention for the manufacture of a medicament for the protection of an animal from an invertebrate pest. The medicament may be in any art recognized dosage forms including oral, topical or parenteral dosage forms.

The invention is also understood to include the crystalline polymorph of Compound 1 designated Form B, or any embodiments of the invention, packaged and presented for the protection of an animal from an invertebrate pest. The compounds of the invention may be packaged and presented as oral, topical or parenteral dosage forms.

The invention is also understood to include a process for manufacturing a composition for protecting an animal from an invertebrate parasitic pest characterized in that the crystalline polymorph of Compound 1 designated Form B, or any embodiments of the invention, are admixed with at least one carrier. The compounds of the invention may be packaged and presented in any art recognized dosage forms including oral, topical or parenteral dosage forms.

Compound 1 is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide and has the following chemical structure:

Compound 1 can exist in more than one crystal form (i.e. polymorph). One skilled in the art will appreciate that a polymorph of Compound 1 can exhibit beneficial effects (e.g., suitability for preparation of useful formulations, improved biological performance) relative to another polymorph or a mixture of polymorphs of the same Compound 1. Differences with respect to chemical stability, filterability, solubility, hygroscopicity, melting point, solid density and flowability can have a significant effect on the development of production methods and formulations, and the quality and efficacy of plant treatment agents.

The molecular structure of Compound 1 can exist as two distinct stereoisomers (i.e. enantiomers). The present invention encompasses a racemic mixture of Compound 1 comprising equal amounts of the two possible enantiomers.

The solid state of Compound 1 has now been discovered to be preparable in more than one solid form. These solid forms include an amorphous solid form, in which there is no long-range order in the positions of molecules (e.g., foams and glasses). These solid forms also include crystalline forms, in which constituent molecules are arranged in an orderly repeating pattern extending in all three spatial dimensions. The term "polymorph" refers to a particular crystalline form of a chemical compound that can exist in more than one crystal structure (e.g., lattice type) in the solid state. Crystalline forms of Compound 1 in this invention relate to embodiments which include a single polymorph (i.e. single crystalline form) and to embodiments which include a mixture of polymorphs (i.e. different crystalline forms). Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of Compound 1 can exhibit beneficial effects (e.g., suitability for preparation of useful formulations, improved biological performance) relative to another polymorph or a mixture of polymorphs of Compound 1. Differences with respect to chemical stability, filterability, solubility, hygroscopicity, melting point, solid density and flowability can have a significant effect on the development of production methods and formulations, and the quality and efficacy of plant treatment agents. Preparation and isolation of particular polymorphs of Compound 1 has now been achieved.

Most of the polymorphs of Compound 1 are pseudopolymorphs (different crystal types that are a result of hydration or solvation). A solvate is a crystal form with either a stoichiometric or non-stoichiometric amount of solvent. A hydrate is a solvate with water as the solvent.

A variety of experimental procedures were conducted to explore the crystalline solid profile for Compound 1. Crystalline solids with eight unique X-ray powder diffraction patterns (XRPD) as well as X-ray amorphous material were generated. The XRPD patterns for the various solids are shown in FIG. 1. Most of the solids are solvates or hydrates.

Solids known to be composed of a single phase are designated as 'Form X' and solids labeled 'Pattern X' may represent a mixture of solid forms. Two polymorphs were identified (Form A and Form B). The crystalline solid profile experiments can be summarized as shown in Scheme 1.

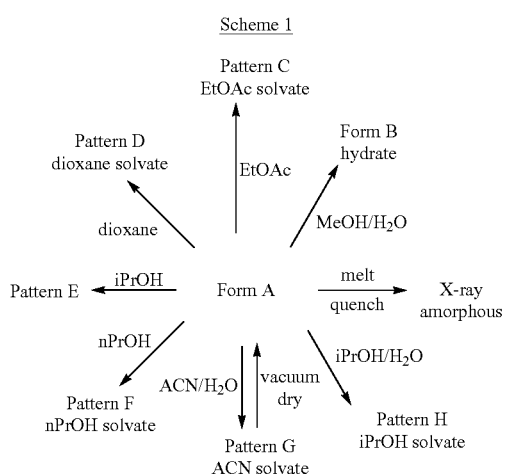

Scheme 1

Compound 1 can exist as an amorphous solid. The XRPD pattern for amorphous solid Compound 1 shows no significant signals and thus is readily distinguished from the patterns of crystalline Compound 1.

The amorphous form of Compound 1 can also be characterized by cyclic Differential Scanning Calorimetry. As described in Characterization Example 2 the glass transition temperature of an amorphous form of Compound 1 was determined to be about 72° C. The amorphous form of Compound 1 is physically unstable and readily crystallized in its pure solid form (shown in Characterization Example 3).

The amorphous solid form was prepared by melting polymorph Form A and then quickly quenching in a dry ice/acetone bath.

One crystalline polymorph form of Compound 1 is designated as Form A. This solid form is a desolvated solvate. A desolvated solvate is formed from a solvate crystal form (containing Compound 1 and solvent molecules) losing the solvent molecules via channels in the crystal under vacuum and heating conditions resulting in a desolvated crystal form with the same molecular packing as the parent solvate crystal form. Form A can be characterized by X-Ray powder diffraction (XRPD) and Differential Scanning Calorimetry (DSC).

The powder X-ray diffraction pattern of polymorph Form A of Compound 1 is shown in FIG. 1. The corresponding 2θ values are tabulated in Table 1 of Characterization Example 1. Polymorph Form A of Compound 1 can be identified by a powder X-ray diffraction pattern having at least the 2θ reflection positions

| 2θ |
|---|
| 16.196 |
| 19.389 |
| 20.324 |
| 21.494 |
| 22.263 |
| 22.797 |
| 23.766 |

-continued

| 2θ |
|---|
| 25.672 |
| 27.492. |

Polymorph Form A of Compound 1 can also be characterized by Differential Scanning Calorimetry. DSC indicates the melting point of polymorph Form A is about 113° C. The details of a DSC experiment are provided in Characterization Example 2. Polymorph Form A is non-hygroscopic and a desolvated solvate related to Pattern G solid which is the acetonitrile solvate of Form A (shown in Characterization Example 3 and 5).

Polymorph Form A of Compound 1 can be prepared by the procedure described in PCT Patent Publication WO 09/025,983 (for example, see Synthesis Example 7). Recrystallization of the crude solid product from acetonitrile usually yields a mixture of Pattern G solid and Form A of Compound 1. Conversion of the mixed solvate/desolvate recrystallized product to Form A can be achieved by vacuum drying (50° C., 4-24 hours).

A second crystalline polymorph form of Compound 1 is designated as Form B. This solid form is a hydrate.

The powder X-ray diffraction pattern of polymorph Form B of Compound 1 is shown in FIG. 1. The corresponding 2θ values are tabulated in Table 2 of Characterization Example 1. Polymorph Form B of Compound 1 can be identified by a powder X-ray diffraction pattern having at least the 2θ reflection positions

| 2θ |
|---|
| 17.433 |
| 18.586 |
| 20.207 |
| 20.791 |
| 21.41 |
| 22.112 |
| 23.182 |
| 24.567 |
| 27.844. |

Polymorph Form B of Compound 1 can also be characterized by Differential Scanning Calorimetry. DSC indicates the melting point of polymorph Form B is about 147° C. The details of a DSC experiment are provided in Characterization Example 2. Polymorph Form B is physically stable and hydrated in its pure solid form (shown in Characterization Example 3). The higher melting point of polymorph Form B is advantageous for use in formulations that involve milling of the active ingredient or a slurry of the active ingredient in liquid carriers.

Slow recrystallization of Form A from methanol/water provided a first purified crop of Form B crystals as described in Preparation Example 1. Polymorph Form B was also produced by slurring polymorph Form A in methanol/water (1:2) at 60° C. for 3 days and then cooling to 22° C. and filtration. Efficient large-scale preparation of Form B is facilitated by the addition of the previously prepared Form B seed crystals to the solution of Compound 1 in methanol/water to cause the product to crystallize in polymorph Form B (see Preparation Examples 2 and 3).

The relative stability of polymorphic Forms A and B of Compound 1 was characterized with interconversion slurry experiments (see Characterization Example 4). The relative physical stability of Compound 1 solid forms is dependent on the solvent used in the slurry experiment. Pattern G solid is the most stable solid form in acetonitrile. Polymorph Form A is a metastable solid form with respect to Pattern G solid in acetonitrile and is sometimes formed in a mixture with Pattern G solid from acetonitrile. Pattern G solid can be converted to polymorph Form A by desolvation via vacuum drying. Polymorph Form B is the most stable solid form in organic solvent/water mixtures especially in methanol/water.

Another crystalline solid form of Compound 1 was designated Pattern C solid. Pattern C solid was characterized by X-Ray powder diffraction and Differential Scanning Calorimetry. The powder X-ray diffraction pattern of Pattern C of Compound 1 is shown in FIG. 1. By DSC Pattern C solid exhibited a single endotherm at 101° C. accompanied by a 9.4% weight loss. Ethyl acetate was detected in the $^1$H NMR of the material indicating that the solid is an ethyl acetate solvate. Pattern C solid was prepared by dissolving Compound 1 in ethyl acetate at 80° C. and then slow cooling to 22° C. and filtration.

Another crystalline solid form of Compound 1 was designated Pattern D solid. Pattern D solid was characterized by X-Ray powder diffraction and Differential Scanning Calorimetry. The powder X-ray diffraction pattern of Pattern D of Compound 1 is shown in FIG. 1. By DSC Pattern D solid exhibited a single endotherm at 105° C. accompanied by a 5.1% weight loss. Dioxane was detected in the $^1$H NMR of the material indicating that the solid is a dioxane solvate. Pattern D solid was prepared by dissolving Compound 1 in dioxane and then fast evaporation under a stream of nitrogen gas at 22° C.

Another crystalline solid form of Compound 1 was designated Pattern E solid. Pattern E solid was characterized only by X-Ray powder diffraction (FIG. 1). Pattern E solid was prepared by dissolving Compound 1 in isopropyl alcohol and then fast evaporation under a stream of nitrogen gas at 22° C.

Another crystalline solid form of Compound 1 was designated Pattern F solid. Pattern F solid was characterized by X-Ray powder diffraction and Differential Scanning Calorimetry. The powder X-ray diffraction pattern of Pattern F of Compound 1 is shown in FIG. 1. By DSC Pattern F solid exhibited a single endotherm at 87° C. accompanied by a 10% weight loss. 1-Propanol was detected in the $^1$H NMR of the material indicating that the solid is a 1-propanol solvate. Pattern F solid was prepared by slurring Compound 1 in 1-propanol/water (9:1) at 40° C. for 4 days and then cooling to 22° C. and filtration.

Another crystalline solid form of Compound 1 was designated Pattern G solid. Pattern G solid was characterized by X-Ray powder diffraction and Differential Scanning Calorimetry. The powder X-ray diffraction pattern of Pattern G of Compound 1 is shown in FIG. 1. By DSC Pattern G solid exhibited a single endotherm at 73° C. accompanied by a 7% weight loss. Acetonitrile was detected in the $^1$H NMR of the material indicating that the solid is an acetonitrile solvate. Pattern G solid was prepared by slurring Compound 1 in acetonitrile/water (1:1) at 40° C. and then slow cooling to 22° C. and filtration. Pattern G solid was consistently prepared from acetonitrile under a variety of recrystallization conditions.

Another crystalline solid form of Compound 1 was designated Pattern H solid. Pattern H solid was characterized by X-Ray powder diffraction and Differential Scanning Calorimetry. The powder X-ray diffraction pattern of Pattern H of Compound 1 is shown in FIG. 1. By DSC Pattern H solid exhibited a single endotherm at 97° C. accompanied by a 3.5% weight loss. Iso-propanol was detected in the $^1$H NMR of the material indicating that the solid is a iso-propanol solvate. Pattern H solid was prepared by slurring Compound 1 in iso-propanol/water (1:1) at 40° C. for 4 days and then cooling to 22° C. and filtration.

Characterization Example 1

X-Ray Powder Diffraction Experiments

Powder X-ray diffraction was used to identify the crystallized phases of Compound 1. X-ray Powder Diffraction (XRPD) analysis were preformed using an Inel XRG-3000 diffractometer equipped with a CPS (Curved Position Sensitive) detector with a 2θ range of 120°. Slits used were 5 mm by 160 μm.

XRPD analysis were also performed using a Shimadzu XRD-6000 with Cu (Kα) radiation.

The radiation was Cu (Kα), 40 kV, 30 mA. Samples were packed powders in an spinning capillary. Data were collected at 2θ angles with an equivalent step size of 0.03 degrees and acquisition time was 300 seconds.

TABLE 1

| 2θ X-ray maxima for Polymorph A of Compound 1 | | | | | |
|---|---|---|---|---|---|
| 2θ | 2θ | 2θ | 2θ | 2θ | 2θ |
| 7.937 | 18.804 | 24.97 | 32.824 | 40.012 | 49.287 |
| 11.233 | 19.389 | 25.672 | 33.443 | 41.447 | 50.022 |
| 13.021 | 20.324 | 27.492 | 34.197 | 43.486 | 75.486 |
| 13.707 | 21.494 | 28.262 | 34.963 | 44.001 | |
| 14.574 | 22.263 | 29.586 | 36.598 | 44.675 | |
| 16.196 | 22.797 | 30.335 | 37.908 | 45.726 | |
| 16.797 | 23.766 | 30.969 | 38.338 | 47.079 | |
| 17.203 | 24.218 | 31.955 | 39.073 | 48.453 | |

TABLE 2

| 2θ X-ray maxima for Polymorph B of Compound 1 | | | | | |
|---|---|---|---|---|---|
| 2θ | 2θ | 2θ | 2θ | 2θ | 2θ |
| 9.393 | 17.433 | 23.182 | 28.828 | 39.273 | 48.635 |
| 11.117 | 18.586 | 24.567 | 29.967 | 40.593 | 50.172 |
| 12.452 | 20.207 | 25.103 | 32.39 | 42.034 | 59.533 |
| 14.023 | 20.791 | 25.853 | 34.83 | 43.237 | |
| 14.744 | 21.41 | 26.942 | 36.301 | 44.906 | |
| 15.361 | 22.112 | 27.844 | 37.286 | 47.078 | |

Characterization Example 2

Differential Scanning Calorimetry Experiments

Differential scanning calorimetry was performed on a Thermal Analysis Q2000 Differential Scanning Calorimeter. A sample was placed in an aluminum DSC pan and the weight accurately recorded. The sample cell was equilibrated at 25° C. or −30° C. and heated under a nitrogen purge at a rate of 10° C./minute up to a final temperature of 250° C. Indium metal was used as the calibration standard.

A cyclic DSC experiment was also preformed using a Thermal Analysis Q2000 Differential Scanning Calorimeter. A sample was placed in an aluminum DSC pan and the weight accurately recorded. The sample cell was equilibrated at 25° C. and heated under a nitrogen purge at a rate of 10° C./minute up to a final temperature of 140° C., rapidly cooled to −40° C. and reheated to a final temperature of 250° C. Indium metal was used as the calibration standard. The glass transition temperature ($T_g$) of amorphous Compound 1 was determined to be 72° C. at half-height.

The DSC curve for polymorph Form A of Compound 1 was observed to exhibit a sharp endotherm at 113° C.

The DSC curve for polymorph Form B of Compound 1 was observed to exhibit a sharp endotherm at 147° C.

Characterization Example 3

Stability Experiments for Solid Forms of Compound 1

The physical stability of the amorphous material was characterized. Amorphous Compound 1 was vapor stressed under acetonitrile at 25° C. for 2 days resulting in the formation of irregular fragments of crystals which were determined to be Pattern G material by XRPD. Amorphous Compound 1 was also slurried in methanol\water (1:1) for 5 days at 60° C. resulting in irregular fragments of crystals determined to be Form B by XRPD. This indicates that the amorphous solid was physically unstable and readily crystallized.

The physical stability of polymorph Form A was characterized. A samples of Form A exposed to 5 to 95% relative humidity at 25° C. (5 hours) showed only negligible weight change indicating the material is non-hygroscopic.

The physical stability of polymorph Form B was characterized. Samples of Form B were stressed under 75% relative humidity (40° C.) and 60% relative humidity (25° C.) for 1 month were also unchanged by XRPD, indicating that Farm B is stable under the conditions tested.

Characterization Example 4

Relative Stability Experiments for Polymorph Form A and Form B

Interconversion slurry experiments were performed in a variety of solvents at different temperatures. Sufficient amounts of Compound 1 were added to solvents in vials so that excess solid remained. The mixtures were agitated in sealed vials at the selected temperature and the solids were isolated by filtration after the selected time and analyzed by XRPD. Compound 1 slurried in acetonitrile for 3 days at 83° C. or for 8 days at 0° C. yielded Pattern G solid. Compound 1 slurried in acetonitrile/water (9:1) for 3 days at 83° C. yielded polymorph Form B. Compound 1 slurried in acetonitrile/water (9:1) for 8 days at 0° C. yielded Pattern G solid.

Characterization Example 5

Vacuum Drying Experiment

Conversion of Pattern G solid to Form A was achieved by vacuum drying (36-68 mtorr) Pattern G solid at 50° C. for 4 hours. Vacuum drying (51 mtorr) at 70° C. for 5 hours caused Pattern G solid to become a solid glass.

Compound 1 can be prepared according to the procedures disclosed in PCT Patent Publications WO 09/025,983) and WO 09/126,668.

Preparation Example 1

Initial Preparation of Polymorph Form B of Compound 1

Crude Compound 1 (10.2 g) was added to boiling methanol (60 mL). Water (12 mL) was slowly added, followed by a small amount of methanol. The heat was removed, the reaction mixture was allowed to cool briefly, and then seed crystals of Compound 1 Form A were added. The reaction mixture was cooled to room temperature (seed crystals were again added until they no longer dissolved), and then further cooled to about 0° C. for 24 h. The reaction mixture was filtered to yield 6.0 g of a white solid melting at 100-105° C. (NMR indicates solvent contamination).

The filtrate from above was allowed to sit for approximately 30 days at room temperature, resulting in the formation of a second crop of crystals. The crystals were isolated by filtration, washed with water, briefly air dried, and finally dried under vacuum at 50° C. to yield 2.9 g of a white solid melting at 144-150° C.

Preparation Example 2

Preparation of Polymorph Form B of Compound 1 from Polymorph Form A

Compound 1 Form A (15.3 g) was added to methanol (120 g) and water (50.4 g). The reaction mixture was heated to 40° C., and after 10 min seed crystals of Compound 1 (Form B) were added. The reaction mixture was stirred at 35° C. for 72 h, cooled to room temperature, and filtered. The isolated solid was dried in a vacuum oven at 50-60° C. to yield 13.4 g of a white solid melting at 147-149° C.

Preparation Example 3

Preparation of Polymorph Form B of Compound 1 Using Seed Crystals

Compound 1 (95 g) was added to methanol (408 g). The mixture was mechanically stirred and heated to 30° C. to dissolve the solid completely. Water (129 g) was added dropwise until the solution was turbid and seed crystals of Form B were added. The mixture was allowed to cool to 25° C. and stirred for 3.5 hours. A thick white solid began to precipitate and the mixture was then heated to 45° C. for 1 hour and cooled to 25° C. over 45 minutes. The mixture was heated again to 45° C. for 50 minutes and then cooled to 25° C. over 40 minutes and filtered. The temperature cycling enables the crystals to grow to a larger size to enable filtration. The crystals were washed with a cold mixture of methanol\water (95 mL of 3:1) and dried in a vacuum oven at 50° C. for 16 hours to give 82 g of a white solid melting at 145-148° C.

Agronomic Formulation/Utility

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible Granules, Tablets and Powders | 0.001-90 | 0-99.999 | 0-15 |
| Oil Dispersions, Aqueous Suspensions | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants;

sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill) Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 1 | 10.0% |
| attapulgite granules (low volatile matter, 0.71/0.30 mm; U.S.S. No. 25-50 sieves) | 90.0% |

Example D

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 1 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| Compound 1 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

| Suspension Concentrate | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| Compound 1 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| Compound 1 | 10.0% |
| fipronil (second active ingredient) | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Agronomic and Nonagronomic Pests

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura* rosaceana Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus vestitus*), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches mono* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae. Also included are eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Forster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compound 1 of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compound 1 of the invention also have activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compound 1 of this invention also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus vari-*

*olarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of Compound 1 of this invention for controlling silverleaf whitefly (*Bemisia argentifolii*). Of note is use of Compound 1 of this invention for controlling western flower thrip (*Frankliniella occidentalis*). Of note is use of Compound 1 of this invention for controlling potato leafhopper (*Empoasca fabae*). Of note is use of Compound 1 of this invention for controlling diamondback moth (*Plutella xylostella*). Of note is use of Compound 1 of this invention for controlling fall armyworm (*Spodoptera frugiperda*).

Agronomic Mixtures/Compositions

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1 and an effective amount of at least one additional biologically active compound or agent and can further comprise at least one of surfactants, solid diluents or liquid diluents. For mixtures of the present invention, the other biologically active compounds or agents can be formulated together with the present compounds, including the compound of Formula 1, to form a premix, or the other biologically active compounds or agents can be formulated separately from the present compounds, including the compound of Formula 1, and the two formulations combined together before application (e.g., in a spray tank) or, alternatively, applied in succession.

Compound 1 of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, at least one additional component selected from the group consisting of surfactants, solid diluents and liquid diluents, and at least one additional biologically active compound or agent. For mixtures of the present invention, the other biologically active compounds or agents can be formulated together with the present compounds, including the compound of Formula 1, to form a premix, or the other biologically active compounds or agents can be formulated separately from the present compounds, including the compound of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bifenthrin, bifenazate, bistrifluoron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, methoxyfenozide, metofluthrin, milbemycin oxime, monocrotophos, nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

One embodiment of biological agents for mixing with compounds of this invention include entomopathogenic bacteria such as *Bacillus thuringiensis*, and the encapsulated delta-endotoxins of *Bacillus thuringiensis* (e.g., Cellcap, MPV, MPVII); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole (see U.S. Pat. No. 6,747,047, PCT Publications WO 2003/015518 and WO 2004/067528) and flubendiamide (see U.S. Pat. No. 6,603,044); nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as acibenzolar, aldimorph, ametoctradin, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamyc in, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penflufen, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pyrazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, tebufloquin, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, valifenalate, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2$^{nd}$ Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1 (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
| --- | --- | --- |
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |

TABLE A-continued

| Invertebrate Pest Control Agent | Mode of Action or Chemical Class | Typical Weight Ratio |
| --- | --- | --- |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |
| (a) | ryanodine receptor ligands | 100:1 to 1:120 |

(a) 3-bromo-1-(3-chloro-2-pyridinyl)-N-[4-cyano-2-methyl-6-[(methylamino)carbonyl]-phenyl]-1H-pyrazole-5-carboxamide Of note is the composition of the present invention wherein the at least one additional biologically active compound or agent is selected from the Invertebrate Pest Control Agents listed in Table A above.

The weight ratios of a compound, including a compound of Formula 1 to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a compound of Formula 1 and an additional invertebrate pest control agent.

TABLE B

| Mixture No. | Cmpd. No. | and | Invertebrate Pest Control Agent |
|---|---|---|---|
| A-1 | 1 | and | Abamectin |
| A-2 | 1 | and | Acetamiprid |
| A-3 | 1 | and | Amitraz |
| A-4 | 1 | and | Avermectin |
| A-5 | 1 | and | Azadirachtin |
| A-6 | 1 | and | Beta-cyfluthrin |
| A-7 | 1 | and | Bifenthrin |
| A-8 | 1 | and | Buprofezin |
| A-9 | 1 | and | Cartap |
| A-10 | 1 | and | Chlorantraniliprole |
| A-11 | 1 | and | Chlorfenapyr |
| A-12 | 1 | and | Chlorpyrifos |
| A-13 | 1 | and | Clothianidin |
| A-14 | 1 | and | Cyfluthrin |
| A-15 | 1 | and | Cyhalothrin |
| A-16 | 1 | and | Cypermethrin |
| A-17 | 1 | and | Cyromazine |
| A-18 | 1 | and | Deltamethrin |
| A-19 | 1 | and | Dieldrin |
| A-20 | 1 | and | Dinotefuran |
| A-21 | 1 | and | Diofenolan |
| A-22 | 1 | and | Emamectin |
| A-23 | 1 | and | Endosulfan |
| A-24 | 1 | and | Esfenvalerate |
| A-25 | 1 | and | Ethiprole |
| A-26 | 1 | and | Fenothiocarb |
| A-27 | 1 | and | Fenoxycarb |
| A-28 | 1 | and | Fenvalerate |
| A-29 | 1 | and | Fipronil |
| A-30 | 1 | and | Flonicamid |
| A-31 | 1 | and | Flubendiamide |
| A-32 | 1 | and | Flufenoxuron |
| A-33 | 1 | and | Hexaflumuron |
| A-34 | 1 | and | Hydramethylnon |
| A-35 | 1 | and | Imidacloprid |
| A-36 | 1 | and | Indoxacarb |
| A-37 | 1 | and | Lambda-cyhalothrin |
| A-38 | 1 | and | Lufenuron |
| A-39 | 1 | and | Metaflumizone |
| A-40 | 1 | and | Methomyl |
| A-41 | 1 | and | Methoprene |
| A-42 | 1 | and | Methoxyfenozide |
| A-43 | 1 | and | Nitenpyram |
| A-44 | 1 | and | Nithiazine |
| A-45 | 1 | and | Novaluron |
| A-46 | 1 | and | Oxamyl |
| A-47 | 1 | and | Pymetrozine |
| A-48 | 1 | and | Pyrethrin |
| A-49 | 1 | and | Pyridaben |
| A-50 | 1 | and | Pyridalyl |
| A-51 | 1 | and | Pyriproxyfen |
| A-52 | 1 | and | Ryanodine |
| A-53 | 1 | and | Spinetoram |
| A-54 | 1 | and | Spinosad |
| A-55 | 1 | and | Spirodiclofen |
| A-56 | 1 | and | Spiromesifen |
| A-57 | 1 | and | Tebufenozide |
| A-58 | 1 | and | Thiacloprid |
| A-59 | 1 | and | Thiamethoxam |
| A-60 | 1 | and | Thiodicarb |
| A-61 | 1 | and | Thiosultap-sodium |
| A-62 | 1 | and | Tralomethrin |
| A-63 | 1 | and | Triazamate |
| A-64 | 1 | and | Triflumuron |
| A-65 | 1 | and | *Bacillus thuringiensis* |
| A-66 | 1 | and | *Bacillus thuringiensis* delta-endotoxin |
| A-67 | 1 | and | NPV (e.g., Gemstar) |
| A-68 | 1 | and | (a) |

(a) 3-bromo-1-(3-chloro-2-pyridinyl)-N-[4-cyano-2-methyl-6-[(methylamino)carbonyl]-phenyl]-1H-pyrazole-5-carboxamide The specific mixtures listed in Table B typically combine a compound of Formula 1 with the other invertebrate pest agent in the ratios specified in Table A.

Agronomic Application

Invertebrate pests are controlled in agronomic and nonagronomic applications by applying the compound of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. The compound of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compound of this invention can also be impregnated into materials for fabricating invertebrate control devices (e.g., insect netting).

Compound 1 of this invention is also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Monograph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

Compound 1 of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

Compound 1 of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nongronomic and Animal Health Utility

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compound and compositions also include the control of pests such as termites that can damage wood or other structural materials used in buildings.

Nonagronomic uses of the present Compound 1 and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present invention are particularly suitable for combating external parasitic or disease transmitting pests. Compound 1 and compositions of the present invention are suitable for systemic and/or non-systemic control of infestation or infection by parasites on animals.

Compound 1 and compositions of the present invention are suitable for combating parasites that infest animal subjects including those in the wild, livestock and agricultural working animals such as cattle, sheep, goats, horses, pigs, donkeys, camels, buffalos, rabbits, hens, turkeys, ducks, geese and bees (e.g., raised for meat, milk, butter, eggs, fur, leather, feathers and/or wool). By combating parasites, fatalities and performance reduction (in terms of meat, milk, wool, skins, eggs, honey, etc.) are reduced, so that applying a composition comprising a compound of the present invention allows more economic and simple husbandry of animals.

Compound 1 and compositions of the present invention are especially suitable for combating parasites that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the inventive compounds can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws, and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Animal Health Pests/Parasites

Examples of invertebrate parasitic pests controlled by administering a parasiticidally effective amount of a compound of this invention to an animal to be protected include ectoparasites (arthropods, acarines, etc) and endoparasites (helminths, e.g., nematodes, trematodes, cestodes, acanthocephalans, etc.).

The disease or group of diseases described generally as helminthiasis is due to infection of an animal host with parasitic worms known as helminths. The term telminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the Helminths, the group of worms described as nematodes causes widespread and at times serious infection in various species of animals. Nematodes that are contemplated to be treated by the compounds of this invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria,* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the Compound 1 of this invention and by the inventive methods include, without limitation, the following genera: *Alaria, Fasciola, Nanophyetus, Opisthorchis, Paragonimus* and *Schistosoma*.

Cestodes that are contemplated to be treated by the Compound 1 of this invention and by the inventive methods include, without limitation, the following genera: *Diphyllobothrium*, Diplydium, Spirometra and *Taenia*.

The most common genera of parasites of the gastrointestinal tract of humans are *Ancylostoma, Necator, Ascaris, Strongyloides, Trichinella, Capillaria, Trichuris*, and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other Helminth genera and species are known to the art, and are also contemplated to be treated by the compounds of the invention. These are enumerated in great detail in *Textbook of Veterinary Clinical Parasitology, Volume 1, Helminths*, E. J. L. Soulsby, F. A. Davis Co., Philadelphia, Pa.; *Helminths, Arthropods and Protozoa*, ($6^{th}$ Edition of Monnig's Veterinary Helminthology and Entomology), E. J. L. Soulsby, The Williams and Wilkins Co., Baltimore, Md.

It is also contemplated that the inventive compound is effective against a number of ectoparasites of animals, e.g., arthropod ectoparasites of mammals and birds although it is also recognized that some arthropods can be endoparasites as well.

Thus, insect and acarine pests include, e.g., biting insects, such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp., and *Aedes* spp.

Mites include *Mesostigmata* spp. e.g., mesostigmatids such as the chicken mite, *Dermanyssus gallinae*; itch or scab mites such as Sarcoptidae spp. for example, *Sarcoptes scabiei*; mange mites such as Psoroptidae spp. including *Chorioptes bovis* and *Psoroptes ovis*; chiggers e.g., Trombiculidae spp. for example the North American chigger, *Trombicula alfreddugesi*.

Ticks include, e.g., soft-bodied ticks including Argasidae spp. for example *Argas* spp. and *Ornithodoros* spp.; hard-bodied ticks including Ixodidae spp., for example *Rhipicephalus sanguineus, Dermacentor variabilis, Dermacentor andersoni, Amblyomma americanum, Ixodes scapularis* and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); Triatominae spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by Compound 1 of the invention. These are enumerated in great detail in *Medical and Veterinary Entomology*, D. S. Kettle, John Wiley & Sons, New York and Toronto; *Control of Arthropod Pests of Livestock: A Review of Technology*, R. O. Drummand, J. E. George, and S. E. Kunz, CRC Press, Boca Raton, Fla.

It is also contemplated that Compound 1 and compositions of this invention may be effective against a number of protozoa endoparasites of animals, including those summarized by Table 3, as follows.

TABLE 3

Exemplary Parasitic Protozoa and Associated Human Diseases

| Phylum | Subphylum | Representative Genera | Human Disease or Disorder |
|---|---|---|---|
| Sarcomastigophora (with flagella, pseudopodia, or both) | Mastigophoratigopora (Flagella) | Leishmania | Visceral, cutaneous and mucocutaneous Infection |
| | | Trypansoma | Sleeping sickness Chagas' disease |
| | | Giardia | Diarrhea |
| | | Trichomonas | Vaginitis |
| | Sarcodina (pseudopodia) | Entamoeba | Dysentery, liver Abscess |
| | | Dientamoeba | Colitis |
| | | Naegleria and Acanthamoeba | Central nervous system and corneal ulcers |
| | | Babesia | Babesiesis |
| Apicomplexa (apical complex) | | Plasmodium | Malaria |
| | | Isospora | Diarrhea |
| | | Sarcocystis | Diarrhea |
| | | Cryptosporidum | Diarrhea |
| | | Toxoplasma | Toxoplasmosis |
| | | Eimeria | Chicken coccidiosis |
| Microspora | | Enterocytozoon | Diarrhea |
| Ciliaphora (with cilia) | | Balantidium | Dysentery |
| Unclassified | | Pneumocystis | Pneumonia |

In particular, Compound 1 of this invention is effective against ectoparasites including: flies such as *Haematobia* (Lyperosia) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola* (Damalinia) *bovis, Bovicola equi, Haematopinus asini, Felicola subrostratus, Heterodoxus spiniger, Lignonathus setosus* and *Tri-*

*chodectes canis*; keds such as *Melophagus ovinus*; mites such as *Psoroptes* spp., *Sarcoptes scabei*, *Chorioptes bovis*, *Demodex equi*, *Cheyletiella* spp., *Notoedres cati*, *Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

Animal Health Mixtures

Biologically active Compound 1 or agents useful in the compositions of the present invention include the organophosphate pesticides. This class of pesticides has very broad activity as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion and phosalone. It is also contemplated to include combinations of the inventive methods and compounds with carbamate type pesticides, including, e.g., carbaryl, carbofuran, aldicarb, molinate, methomyl, carbofuran, etc., as well as combinations with the organochlorine type pesticides. It is further contemplated to include combinations with biological pesticides, including repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *bacillus thuringensis*, chlorobenzilate, formamidines (e.g., amitraz), copper compounds (e.g., copper hydroxide and cupric oxychloride sulfate), cyfluthrin, cypermethrin, dicofol, endosulfan, esenfenvalerate, fenvalerate, lambda-cyhalothrin, methoxychlor and sulfur.

Of note are additional biologically active compounds or agents selected from art-known anthelmintics, such as, for example, avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole) and praziquantel.

Other biologically active compounds or agents useful in the compositions of the present invention can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Of note are biologically active compounds or agents useful in the compositions of the present invention selected from the antiparasitic class of avermectin compounds. As stated above, the avermectin family of compounds is a series of very potent antiparasitic agents known to be useful against a broad spectrum of endoparasites and ectoparasites in mammals.

A preferred compound for use within the scope of the present invention is ivermectin.

Ivermectin is a semi-synthetic derivative of avermectin and is generally produced as a mixture of at least 80% 22,23-Dihydroavermectin $B_{1a}$ and less than 20% 22,23-Dihydroavermectin $B_{1b}$. Ivermectin is disclosed in U.S. Pat. No. 4,199,569.

Abamectin is an avermectin that is disclosed as Avermectin $B_{1a}/B_{1b}$ in U.S. Pat. No. 4,310,519. Abamectin contains at least 80% of avermectin $B_{1a}$ and not more than 20% of avermectin $B_{1b}$.

Another preferred avermectin is Doramectin, also known as 25-Cyclohexyl-avermectin $B_1$. The structure and preparation of Doramectin is disclosed in U.S. Pat. No. 5,089,480.

Another preferred avermectin is Moxidectin. Moxidectin, also known as LL-F28249 alpha, is known from U.S. Pat. No. 4,916,154.

Another preferred avermectin is Selamectin. Selamectin is 25-Cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a Milbemycin producing strain of *Streptomyces*. The microorganism, the fermentation conditions and the isolation procedures are more fully described in U.S. Pat. No. 3,950,360 and U.S. Pat. No. 3,984,564.

Emamectin (4"-deoxy-4"-epi-Methylaminoavermectin $B_1$), which can be prepared as described in U.S. Pat. No. 5,288,710 or U.S. Pat. No. 5,399,717, is a mixture of two homologues, 4"-deoxy-4"-epi-methylaminoavermectin $B_{1a}$ and 4"-deoxy-4"-epi-methylaminoavermectin $B_{1b}$. Preferably, a salt of Emamectin is used. Non-limiting examples of salts of Emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is Emamectin benzoate.

Eprinomectin is chemically known as 4"-epi-acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds: imidazo[1,2-b]pyridazine compounds as described by U.S. application Ser. No. 11/019,597, filed on Dec. 22, 2004; 1-(4-mono and di-halomethylsulphonylphenyl)-2-acylamino-3-fluoropropanol compounds, as described by U.S. application Ser. No. 11/018,156, filed on Dec. 21, 2004; trifluoromethanesulfonanilide oxime ether derivatives, as described by U.S. application Ser. No. 11/231,423, filed on Sep. 21, 2005; and n-[(phenyloxy)phenyl]-1,1,1-trifluoromethanesulfonamide and n-[(phenylsulfanyl)phenyl]-1,1,1-trifluoromethanesulfonamide derivatives, as described by U.S. Provisional Application Ser. No. 60/688,898, filed on Jun. 9, 2005.

The compositions of the present invention may also further comprise a flukicide. Suitable flukicides include, for example, Triclabendazole, Fenbendazole, Albendazole, Clorsulon and Oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed herein below.

One useful antibiotic is Florfenicol, also known as D-(threo)-1-(4-methylsulfonylphenyl)-2-dichloroacetamido-3-fluoro-1-propanol. Another preferred antibiotic compound is D-(threo)-1-(4-methylsulfonyphenyl)-2-difluoroacetamido-3-fluoro-1-propanol. Another useful antibiotic is Thiamphenicol. Processes for the manufacture of these antibiotic compounds, and intermediates useful in such processes, are described in U.S. Pat. No. 4,311,857; U.S. Pat. No. 4,582,918; U.S. Pat. No. 4,973,750; U.S. Pat. No. 4,876,352; U.S. Pat. No. 5,227,494; U.S. Pat. No. 4,743,700; U.S. Pat. No. 5,567,844; U.S. Pat. No. 5,105,009; U.S. Pat. No. 5,382,673; U.S. Pat. No. 5,352,832; and U.S. Pat. No. 5,663,361. Other florfenicol analogs and/or prodrugs have been disclosed and such analogs also can be used in the compositions and methods of the present invention (see e.g., U.S. Patent Application Publication No: 2004/0082553, and U.S. patent application Ser. No. 11/016,794).

Another useful antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695.

Another useful antibiotic for use in the present invention is Tulathromycin. Tulathromycin may be identified as 1-oxa-6-azacyclopentadecan-15-one, 13[(2,6-dideoxy-3-C-methyl-3-O-methyl-4-C-[(propylamino)methyl]-alpha-L-ribo-hexopyranosyl]oxy]-2-ethyl-3,4,10-trihydroxy-3,5,8,10,12,14-hexamethyl-1-11-[[3,4,6-trideoxy-3-(dimethylamino)-beta-D-xylo-hexopyranosyl]oxy]-, (2R,3S,4R,5R,8R,10R,11R,12S,13S,14R). Tulathromycin may be prepared in accordance with the procedures set forth in U.S. Patent Publication No. 2003/0064939 A1.

Further antibiotics for use in the present invention include the cephalosporins such as, for example, Ceftiofur, Cefquinome, etc. The concentration of the cephalosporin in the formulation of the present invention optionally varies between about 1 mg/ml to 500 mg/ml.

Another useful antibiotic includes the fluoroquinolones, such as, for example, Enrofloxacin, Danofloxacin, Difloxacin, Orbifloxacin and Marbofloxacin. In the case of Enrofloxacin, it may be administered in a concentration of about 100 mg/ml. Danofloxacin may be present in a concentration of about 180 mg/ml.

Other useful macrolide antibiotics include compounds from the class of ketolides, or, more specifically, the azalides. Such compounds are described in, for example, U.S. Pat. No. 6,514,945, U.S. Pat. No. 6,472,371, U.S. Pat. No. 6,270,768, U.S. Pat. No. 6,437,151, U.S. Pat. No. 6,271,255, U.S. Pat. No. 6,239,112, U.S. Pat. No. 5,958,888, U.S. Pat. No. 6,339,063 and U.S. Pat. No. 6,054,434.

Other useful antibiotics include the tetracyclines, particularly Chlortetracycline and Oxytetracycline. Other antibiotics may include β-lactams such as penicillins, e.g., Penicillin, Ampicillin, Amoxicillin, or a combination of Amoxicillin with Clavulanic acid or other beta lactamase inhibitors.

Animal Health Formulation/Application

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal) or implants; by nasal administration; by topical administration, for example, in the form of immersion or dipping, spraying, washing, coating with powder, or application to a small area of the animal, and through articles such as neck collars, ear tags, tail bands, limb bands or halters which comprise compounds or compositions of the present invention.

Compound 1 of the present invention, or a suitable combination of such compound, may be administered directly to the animal subject and/or indirectly by applying it to the local environment in which the animal dwells (such as bedding, enclosures, or the like). Direct administration includes contacting the skin, fur or feathers of a subject animal with the compound, or by feeding or injecting the compound into the animal.

Compound 1 of the present invention may be administered in a controlled release form, e.g., in a subcutaneous slow release formulation, or in the form of a controlled release device affixed to an animal such as a fleacollar. Collars for the controlled release of an insecticide agent for long term protection against flea infestation in a companion animal are art-known, and are described, for example, by U.S. Pat. No. 3,852,416, U.S. Pat. No. 4,224,901, U.S. Pat. No. 5,555,848 and U.S. Pat. No. 5,184,573.

Typically a parasiticidal composition according to the present invention comprises a mixture of a compound of Formula 1 with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of the invention and at least one carrier.

For parenteral administration including intravenous, intramuscular and subcutaneous injection, a compound of the present invention can be formulated in suspension, solution or emulsion in oily or aqueous vehicles, and may contain adjuncts such as suspending, stabilizing and/or dispersing agents. The compounds of the present invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compound may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, Compound 1 of the present invention may also be formulated as a depot preparation. Such long acting formulations may be administered by implantation (for example, subcutaneously or intramuscularly) or by intramuscular or subcutaneous injection. Compound 1 of the present invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, Compound 1 of the present invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Compound 1 of the present invention has been discovered to have favorable pharmacokinetic and pharmacodynamic properties providing systemic availability from oral administration and ingestion. Therefore after ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a compound of the present invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compound of Formula 1 may also be formulated in rectal compositions such as suppositories or retention enemas, using, e.g., conventional suppository bases such as cocoa butter or other glycerides.

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present invention and one or more topically suitable carriers. In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Carriers in such formulations include propylene glycol, paraffins, aromatics, esters such as isopropyl myristate, glycol ethers, alcohols such as ethanol, n-propanol, 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a crystallization inhibitor or a dispersant known from the pharmaceutical or cosmetic industry also to be present.

A pour-on formulation may also be prepared for control of parasites in an animal of agricultural worth. The pour-on formulations of this invention can be in the form of a liquid, powder, emulsion, foam, paste, aerosol, ointment, salve or gel. Typically, the pour-on formulation is liquid. These pour-on formulations can be effectively applied to sheep, cattle, goats, other ruminants, camelids, pigs and horses. The pour-on formulation is typically applied by pouring in one or several lines or in a spot-on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race. The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention typically include an antioxidant, such as BHT (butylated hydroxytoluene). The antioxidant is generally present in amounts of at 0.1-5% (wt/vol). Some of the formulations require a solubilizer, such as oleic acid, to dissolve the active agent, particularly if spinosad is used. Common spreading agents used in these pour-on formulations are: IPM, IPP, caprylic/capric acid esters of saturated $C_{12}$-$C_{18}$ fatty alcohols, oleic acid, oleyl ester, ethyl oleate, triglycerides, silicone oils and DPM. The pour-on formulations of this invention are prepared according to known techniques. Where the pour-on is a solution, the parasiticide/insecticide is mixed with the carrier or vehicle, using heat and stirring where required. Auxiliary or additional ingredients can be added to the mixture of active agent and carrier, or they can be mixed with the active agent prior to the addition of the carrier. If the pour-on is an emulsion or suspension, these formulations are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a compound of Formula 1 is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation.

For oral administration to homeothermic animals, the daily dosage of Compound 1 of the present invention typically ranges from about 0.01 mg/kg to about 100 mg/kg, more typically from about 0.5 mg/kg to about 100 mg/kg, of animal body weight. For topical (e.g., dermal) administration, dips and sprays typically contain from about 0.5 ppm to about 5000 ppm, more typically from about 1 ppm to about 3000 ppm, of Compound 1 of the present invention.

What is claimed is:

1. A crystalline polymorph of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide designated Form B characterized by a powder X-ray diffraction pattern having at least the 2θ reflection positions

| 2θ |
|---|
| 17.433, |
| 18.586, |
| 20.207, |
| 20.791, |
| 21.41, |
| 22.112, |
| 23.182, |
| 24.567 and |
| 27.844. |

2. A composition comprising the polymorph Form B of claim 1 and at least one additional component selected from the group consisting of surfactants, solid diluents and liquid diluents, said composition optionally further comprising at least one additional compound or agent, wherein said additional compound or agent is biologically active.

3. A composition for protecting an animal from an invertebrate parasitic pest comprising a parasiticidally effective amount of the polymorph Form B of claim 1 and at least one carrier.

4. The composition of claim 3 in a dosage form for oral administration.

5. A method for controlling an invertebrate pest comprising contacting the invertebrate pest or its environment with a biologically effective amount of the polymorph Form B of claim 1.

6. The method of claim 5 wherein the environment is a plant.

7. The method of claim 5 wherein the environment is an animal.

* * * * *